United States Patent [19]

Sardam

[11] Patent Number: 4,735,608

[45] Date of Patent: Apr. 5, 1988

[54] APPARATUS FOR STORING AND RECONSTITUTING ANTIBIOTICS WITH INTRAVENOUS FLUIDS

[75] Inventor: William W. Sardam, Balboa Island, Calif.

[73] Assignee: Del F. Kahan, Costa Mesa, Calif. ; a part interest

[21] Appl. No.: 863,120

[22] Filed: May 14, 1986

[51] Int. Cl.[4] .......... A61M 37/00

[52] U.S. Cl. .......... 604/89; 604/84; 604/86; 604/88; 604/82; 604/411

[58] Field of Search .......... 604/82, 87, 88, 89, 604/91, 246, 248, 411, 905

[56] References Cited

U.S. PATENT DOCUMENTS

| | | | |
|---|---|---|---|
| 2,022,109 | 11/1935 | Earp | 221/60 |
| 2,138,992 | 12/1938 | Baker | 221/60 |
| 2,693,189 | 11/1954 | Ryan | 128/272 |
| 3,163,337 | 12/1964 | Wilson | 222/534 |
| 3,323,774 | 6/1967 | Wilson | 604/248 |
| 3,554,256 | 1/1971 | Anderson | 150/8 |
| 3,776,229 | 12/1973 | McPhee . | |
| 3,976,068 | 8/1976 | Lundquist . | |
| 3,993,066 | 11/1976 | Virag . | |
| 4,136,693 | 1/1979 | Dyke | 604/248 |
| 4,180,072 | 12/1979 | Sneider | 604/88 |
| 4,181,246 | 1/1980 | Norris | 222/548 |
| 4,265,760 | 5/1981 | Abel et al. | 210/282 |
| 4,320,770 | 3/1982 | Etherington et al. | 128/766 |
| 4,334,535 | 6/1982 | Wilson et al. . | |
| 4,338,933 | 7/1982 | Bayard et al. | 604/411 |
| 4,411,662 | 10/1983 | Pearson | 604/905 |
| 4,432,750 | 2/1984 | Estep | 604/4 |
| 4,467,588 | 8/1984 | Carveth | 604/87 |
| 4,534,758 | 8/1985 | Akers et al. | 604/411 |
| 4,552,155 | 11/1985 | Etherington et al. | 128/766 |
| 4,589,879 | 5/1986 | Pearson | 604/88 |

*Primary Examiner*—C. Fred Rosenbaum
*Assistant Examiner*—Gene B. Kartchner
*Attorney, Agent, or Firm*—Klein & Szekeres

[57] ABSTRACT

A container for intravenous fluid has a triangular cross-section to permit improved utilization of space during packaging of several containers in boxes or cartons, and a first opening sealed by a membrane seal which can be pierced with the spike of a conventional intravenous set. A second opening of the container is surrounded with a neck portion forming a joint to which an intermediate member is pivotably mounted. The intermediate member includes a hollow cylindrical portion having two circumferential ribs which are adapted to hold the neck of a standard small vial containing solid antibiotics and the like. The intermediate member also includes an internally mounted hollow spike so that the seal of the antibiotic vial is penetrated by the spike when the vial is mounted to the intermediate member. The duct of the spike of the intermediate member is not aligned with the second opening of the container until the intermediate member is rotated or pivoted into an extreme position. Fluid communication between the vial and the container is established only when it is so desired by a user, typically before administration of the reconstituted antibotic to a patient.

26 Claims, 3 Drawing Sheets

FIG. 1
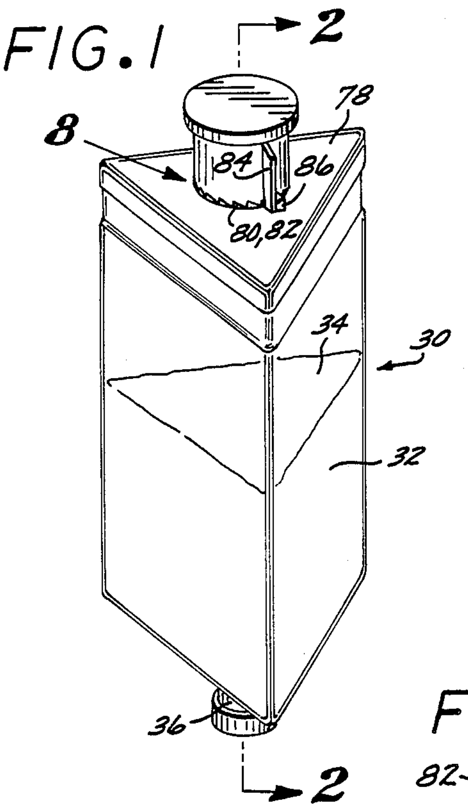
FIG. 2
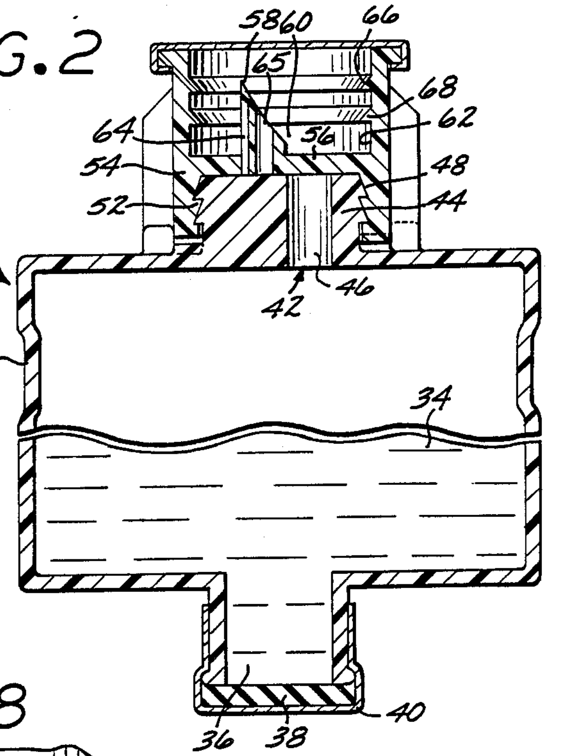
FIG. 8
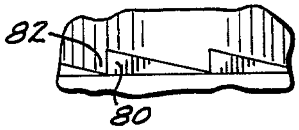
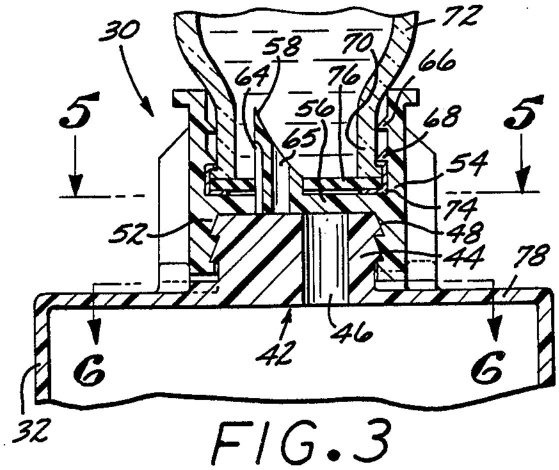
FIG. 3
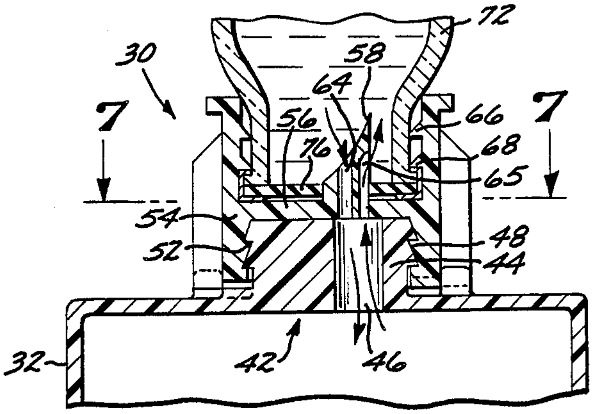
FIG. 4
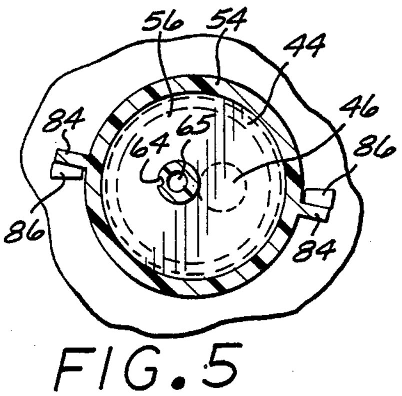
FIG. 5
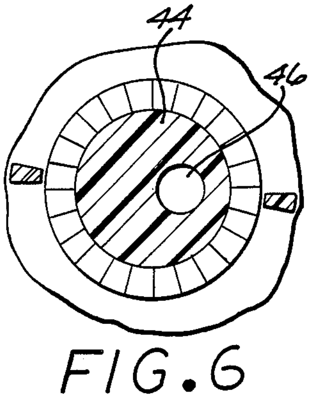
FIG. 6
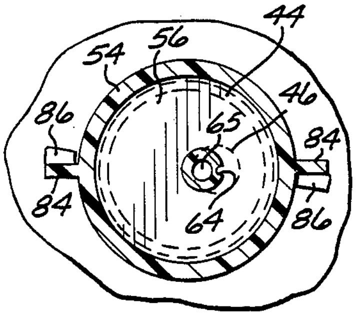
FIG. 7

APPARATUS FOR STORING AND RECONSTITUTING ANTIBIOTICS WITH INTRAVENOUS FLUIDS

BACKGROUND OF THE INVENTION

1. Field of the Invention

The present invention is directed to an intravenous container in combination with separate containers for medicinal agents, such as antibiotics to be reconstituted with the intravenous fluid, and to novel means for jointly storing the two containers and intermixing their contents before administration to a patient.

2. Brief Description of the Prior Art

Containers for intravenous fluids, such as saline or glucose solutions, are well known in the prior art. Moreover, various devices for administering the intravenous fluids with or without medication, nutrients, vitamins, and the like, are also well known in the art.

With regard to some medicinal agents, the prior art has, however, experienced particular difficulty, in that these medicinal agents lose their therapeutic effectiveness, and may even become toxic, when they are dissolved in or admixed with the intravenous fluid for a prolonged period of time. Specifically, but not exclusively, certain antibiotics are stable for prolonged periods of time only in the solid state; once dissolved in an intravenous fluid they must be refrigerated or promptly administered to a patient. In this connection, the common practice in the art of dissolving an antibiotic (or other medicinal agent, such as a chemotherapy drug) in the intravenous fluid, just before administration to a patient, is usually termed "reconstituting" the antibiotic.

In accordance with what is perhaps the most traditional method of "reconstituting", a relatively small volume of intravenous fluid is withdrawn from a container for the fluid with a hypodermic needle and syringe, and the withdrawn fluid is injected through a resilient membrane seal into a small container or vial for the solid antibiotic. Then the solid antibiotic is dissolved in the injected fluid. Thereafter, the antibiotic solution is again withdrawn from the vial with a hypodermic syringe and needle.

Sometimes the antibiotic solution, having been obtained in the above-described manner, is directly injected into a patient. Many times, however, for medical reasons it is desired to dilute the antibiotic (or other medicinal agent or nutrient) solution with more intravenous fluid, and to slowly intravenously infuse the diluted solution to the patient through an intravenous administration (i.v.) set. For this purpose, the freshly obtained, relatively concentrated antibiotic (or other medicinal agent or nutrient) solution is usually injected through another self-sealing resilient membrane seal to a manufacturer's "minibag" or like intravenous bottle or bag containing a larger volume (approximately 50 to 100 ml) of the intravenous fluid. After mixing, the resulting more dilute antibiotic (or other medicinal agent or nutrient) solution is slowly infused into the patient through one or more i.v. sets which are hooked up to the manufacturer's "minibag" or like bottle or bag.

Those skilled in the art know well that the foregoing steps and manipulations must be performed without jeopardizing the sterility of the substances infused to the patient. Those skilled in the art also recognize that the more steps are involved in manipulating the substances, the greater is the chance for contamination, and for harmful or even fatal consequences to the patient.

Because the dissolution of solid or lypholized antibiotics (and of other substances) and subsequent dilution and administration to patients is performed routinely and in large numbers in virtually all hospitals in the United States of America and in other industrialized countries, the procedure involved must not only be safe, but also needs to be fast and relatively inexpensive.

The prior art has developed several devices and methods in an attempt to satisfy the foregoing requirements.

More particularly, one prior art device, designed to simplify the above-summarized manual procedure of drug dissolution and subsequent dilution, is sold by IVAC Corporation under the CRIS (Controlled Release Infusion System) mark. This device comprises a valve fitting controlled by a rotatable dial. The valve fitting includes a hollow spike surrounded by suitable plastic grips to engage the neck of a substantially standard small (5 to 15 ml) container for the solid antibiotic. The valve fitting includes two connections fluidly connecting the valve respectively to a manufacturer's "minibag", bottle, or large volume bottle, or plastic bag, and to an intravenous set. Before the valve fitting is used, the drug in the small container is dissolved by injection of a small amount (commonly 5 to 20 ml) intravenous fluid. Thereafter, the small bottle is connected to the valve fitting in a position where the hollow spike establishes fluid communication with the valve, and the plastic grips hold the small container in place. The manufacturer's "minibag", bottle, large volume bottle, or plastic bag is connected to the valve fitting as the source of the intravenous fluid which is used to dilute the drug solution. The interior design of the valve fitting is such that the inflow of the drug solution to the stream of intravenous fluid flowing through the valve may be closed-off entirely. Alternatively, the drug solution from the small vial is slowly "leaked" through the valve fitting, so that the drug solution attains large dilution by the intravenous fluid. Disadvantages of this (CRIS) system include the need for separately dissolving the drug in the small container before the small container is affixed to the valve fitting, and the high cost of the valve fitting itself. Each valve fitting, of course, should be attached only once to a large volume bottle, or plastic bag, and for safety reasons should be discarded after such use.

Still another prior art system, made by American McGaw, utilizes a plastic adapter which has a hollow spike and a tube in fluid communication with the spike. The spike is surrounded by plastic grips designed to grab and hold small standard containers or vials for drugs, such as the above-mentioned 5 to 15 ml standard size vials for solid reconstitutable antibiotics. The tube is designed to penetrate the plug of a manufacturer's specially designed "minibag". In accordance with this system, the small container is connected with the "minibag", and the drug is dissolved by adding part of the intravenous solution contained in the bag. Thereafter, the drug solution is transferred back from the vial through the tube to the bag for subsequent infusion to the patient. Disadvantages of the just-described system include the system's relatively high cost and that the process of inserting the tube into the "minibag" is somewhat awkward and requires substantial manual dexterity.

A third system relatively widely used in the prior art is distributed by Abbott Laboratories. This system requires a "custom" small container or vial and a "custom" bag, in the sense that the vial and the bag must have matching screw thread connections. Fluid communication is established between the small vial for the antibiotic (or other drug) and the bag containing the intravenous fluid when the vial is threaded into the matching receptacle of the bag. Besides its cost, the disadvantage of this system is that the system cannot be used unless the required drug is available in the requisite custom vial.

In light of the foregoing, there is still need in the art for an improved system or apparatus which permits reconstitution of antibiotics (or other drugs) with an intravenous fluid and subsequent administration of a diluted antibiotic solution to a patient with a minimum of manipulative steps and with minimal possibility for contamination. The present invention provides such a system or apparatus.

In addition to the above-summarized practical examples of prior art, the following patents disclose subject matter which comprises relevant background or is otherwise "of interest" to the present invention: U.S. Pat. Nos. 3,544,256; 3,163,337; 4,432,750; 2,022,109; 2,138,992; 2,693,189; 3,776,229; 3,993,066; 3,976,068; 4,181,246; 4,334,535; and 4,265,760.

SUMMARY OF THE INVENTION

It is an object of the present invention to provide a system or apparatus for reconstituting antibiotics and the like drugs or nutrients, and diluting the same with a relatively large volume of intravenous fluid for subsequent administration to a patient.

It is another object of the present invention to provide a system or apparatus which meets the above-noted objectives and performs the above-noted functions in a minimum number of manipulative steps so as to minimize the chances for accidentally contaminating the fluids to be administered to the patient.

It is still another object of the present invention to provide a system or apparatus which meets the above-noted objectives and permits handling of a single container for the intravenous fluid together with a single vial for antibiotic or like drug, the single drug vial being dedicated to be used in conjunction with the intravenous fluid contained in the single container.

It is yet another object of the present invention to provide a system or apparatus which meets the above-noted objectives and which is capable of utilizing substantially standard small vials or containers for the antibiotic or like drug.

It is a further object of the present invention to reduce waste of antibiotics or other drugs by allowing preparation of the drug for administration while still preventing contact between the drug and the diluent until immediately prior to administration, and thereby providing effective means for reconstitution, for example, at the patient's bedside.

It is still a further object of the invention to provide a closed system within which chemotherapeutic or other toxic drugs may be reconstituted and administered without exposing pharmacists, technicians, or nurses to such toxic drugs through "aerosoling" or other contact during transfer of the drug.

It is yet a further object of the invention to allow preparation of an antibiotic or other drug for administration at a centralized facility, such as a hospital pharmacy, or home health care company pharmacy, and subsequent transportation without refrigeration or freezing, to a patient's home where the drug can be easily and quickly reconstituted just prior to administration.

The foregoing and other objects and advantages are attained by a system or apparatus including a container for an intravenous fluid, which container has a first opening sealed with a first membrane. The first membrane is of the type which may be pierced and penetrated with a sharp spike of a secondary intravenous set, whereby the contents of the first container can be slowly drained through the intravenous set in the process of administering the contents to a patient.

The container of the apparatus or system has a second opening equipped with means for capturing and holding the neck of a second container or vial containing an antibiotic or other drug, vitamin, medication, or nutrient. In this regard, the means are preferably configured for capturing and holding the neck of standard small vials for solid antibiotics of the type which have an internal volume of approximately 5 to 20 ml, and which have a pierceable second membrane seal affixed to the vial with a metal band.

The means for holding the vial also include a spike or the like to penetrate the second membrane seal, without, however, establishing fluid communication between the container for the intravenous fluid and the vial. Fluid communication between the container for the intravenous fluid and the vial is established only at the option of an operator through a rotating, pivoting, or like movement of the means which then opens passageways for the intravenous fluid to flow into the vial to reconstitute the drug or the like therein, and for the reconstituted solution to flow back into the container for the intravenous fluid.

The features of the present invention can be best understood, together with further objects and advantages by reference to the following description, taken in conjunction with the accompanying drawings, wherein like numerals designate like parts.

BRIEF DESCRIPTION OF THE DRAWINGS

FIG. 1 is a perspective view of a first preferred embodiment of the apparatus of the present invention;

FIG. 2 is a cross-sectional view of the first preferred embodiment, the view being taken on lines 2,2 of FIG. 1;

FIG. 3 is a partial cross-sectional view of the first preferred embodiment having a substantially standard small vial for antibiotics or the like, mounted to the first preferred embodiment in a first position where there is no fluid communication between the intravenous bottle of the first embodiment and the standard vial;

FIG. 4 is a partial cross-sectional view of the first preferred embodiment having the substantially standard small vial for antibiotics or the like, mounted to the first preferred embodiment in a second position where there is fluid communication between the intravenous bottle of the first embodiment and the standard vial;

FIG. 5 is a cross-sectional view taken on lines 5,5 of FIG. 3;

FIG. 6 is a cross-sectional view taken on lines 6,6 of FIG. 3;

FIG. 7 is a cross-sectional view taken on lines 7,7 of FIG. 4;

FIG. 8 is a detailed view of the area indicated on FIG. 1 by arrow 8;

DESCRIPTION OF THE PREFERRED EMBODIMENTS

Figure 9:
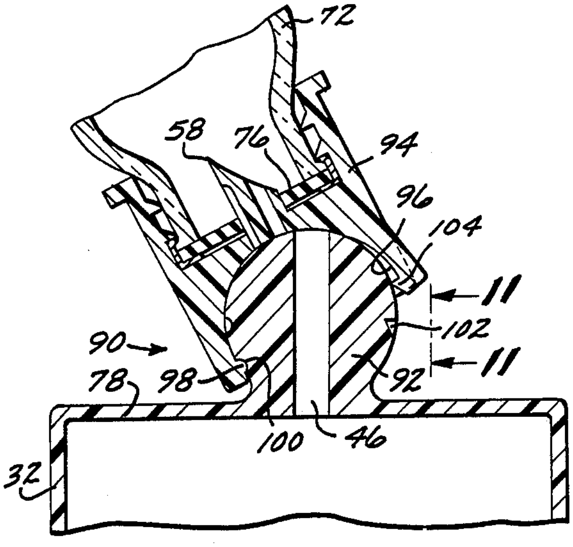
FIG. 9 is a partial cross-sectional view of a second preferred embodiment of the apparatus of the present invention having a standard small vial for antibiotics or the like, mounted to the second preferred embodiment in a first position where there is no fluid communication between the intravenous bottle of the second embodiment and the standard vial.

The following specification taken in conjunction with the drawings sets forth the preferred embodiments of the present invention. The embodiments of the invention disclosed herein are the best modes contemplated by the inventor for carrying out his invention in a commercial environment, although it should be understood that several modifications can be accomplished within the scope of the present invention.

Referring now to FIGS. 1-8 of the appended drawings, a first preferred embodiment 30 of the apparatus or system of the present invention is disclosed. The first preferred embodiment 30 includes a container or bottle 32 which typically contains between approximately 50 to 1000 ml of an intravenous fluid 34. In this regard, it is noted that the container or bottle 32 of the present invention corresponds in many respects to the so-called "manufacturer's piggyback bottles" of the prior art. In other words, the container 32 of the apparatus of the present invention has many, hereinafter-described novel features. Nevertheless, one of its principal functions is in accordance with standard practice in the art to provide a volume of intravenous fluid which is used to reconstitute and dilute an antibiotic, drug, vitamin, or like substance, and which is thereafter intravenously administered to a patient without further transfer into another storage container. The intravenous fluid 34 may be standard sterile water, saline, or dextrose solution. In this regard, it should be clearly understood that the present invention is not limited either by the nature or volume of the solution 34 contained in the bottle 32.

The container or bottle 32 has a first opening 36, shown on FIGS. 1 and 2. The first opening 36 is sealed, in accordance with standard practice in the art, with a pierceable seal or membrane 38, that can be penetrated by a conventional spike (not shown) of a standard intravenous (i.v.) set (not shown). As is well known in the art, the contents of the bottle 32 are administered to a patient (not shown) through such an i.v. set (not shown). The nature of the seal 38 and of the entire structure sealing the first opening 36 of the container 32 of the present invention is substantially conventional. Thus, the sealing structure, shown on FIGS. 1 and 2, includes a protective cover 40 for the resilient elastic seal 38.

Referring still to FIGS. 1 through 8 showing the first preferred embodiment 30, the container 32 has a second opening 42 which, together with its associated structure, comprises a significant novel aspect of the present invention. Referring specifically to FIG. 2, the second opening, together with the associated structure 42, includes a substantially cylindrical neck portion 44 and a relatively narrow duct or flow channel 46 incorporated in the neck portion 44. The cylindrical neck portion 44 protrudes upwardly from the container 32 and, for the reasons which become apparent from the description below, can be regarded as a hinge base member.

The exterior cylindrical surface 48 of the neck 44 is threaded or ribbed and engages matching female threads or depressions 52 of an intermediate member 54. The intermediate member 54 is thus threadedly mounted to the neck 44. A cross-plate 56 is disposed in the intermediate member 54, just above the neck 44. The cross-plate 56 supports a hollow spike 58 disposed within an interior cavity 60, defined by the interior cylindrical walls 62 of the intermediate member 54. In the normal mounting position of the intermediate member 54 to the neck 44, the two ducts 64 and 65 of the hollow spike 58 are not aligned with the duct or flow channel 46 of the neck 44. This is shown on FIGS. 2, 3, and 5.

The interior walls 62 of the intermediate member 54 include a pair of parallel disposed circumferential ribs or protrusions, bearing the reference numerals 66 and 68. The purpose of the ribs 66 and 68 is to guide and hold the neck 70 of a small container or vial 72, as is shown in FIGS. 3 and 4. For these reasons, the first circumferential rib 66 is less firm or rigid than the second circumferential rib 68 which, as shown on FIGS. 3 and 4, engages and holds the metal band 74 containing neck 70 of the small antibiotic vial 72. In alternative embodiments (not shown) a single rib, rather than two ribs, may be used.

In this regard, it is noted that the small antibiotic vial is "standard" in the industry, in the sense that most drug manufacturers distribute solid antibiotics (and like substances which must be reconstituted prior to intravenous administration to patients) in standard size vial of approximately 5 to 20 ml volume capacity. Moreover, the "standard" antibiotic vials have a "standard" configuration for the neck 70 and for the metal band 74 which holds a resilient, pierceable, substantially standard seal 76 to the neck 70 of the vial 72. FIGS. 3 and 4 show the standard antibiotic vial 72 mounted to the intermediate member 54 with the spike 58 having penetrated the seal 76. It is a novel feature of the present invention that fluid communication between the interior of the container 32 and the vial 72 is not established immediately when the vial 72 is mounted to the intermediate member 54.

Continuing still with the description of the first preferred embodiment 30, the upper surface 78 of the container 32 includes ratchet teeth 80 matched by complementary ratchet teeth 82 provided in the intermediate member 54. The ratchet teeth 80 immediately surround the cylindrical neck 44. This is perhaps best illustrated on FIG. 8. A pair of tabs or ears 84 are provided on the exterior of the intermediate member 54, and a pair of corresponding stop members or protrusions 86 are located on the upper surface 78 of the container 32.

The configuration and location of the ratchet teeth 80 and 82, of the ears 84 and stop members 86 is such that the intermediate member 54 can be turned on the neck or hinge base member 44 only in one direction, and only until the ears 84 engage the stop members 86. The intermediate member 54 is shown in the turned, second position on FIGS. 4 and 7. In this second position of the intermediate member 54, the ducts 64 and 65 of the spike 58 are aligned with the duct or flow channel 46 of the container 32. Therefore, in the second position of the intermediate member 54 relative to the container 32, there is fluid communication between the container 32 and the antibiotic vial 72. Once the fluid communication between the container 32 and the vial 72 has been established, the cooperating ratchet teeth 80 and 82 prevent the intermediate member 54 from being turned in the opposite direction, so that the fluid communication cannot be broken, and the positioning of the intermediate member 54 cannot be reversed. In still other embodiments (not shown) the ratchet teeth may be replaced by a bayonet slot (not shown) and the stop members may be replaced by appropriate serrations (not shown).

Referring now primarily to FIG. 1 of the appended drawings, an additional novel feature of the apparatus of the present invention is disclosed in that the bottle or container 32 has a triangular cross-section taken in a plane which is perpendicular to the longitudinal axis of the bottle 32. This particular configuration of the bottle 32 facilitates stacking of a plurality of such bottles 32 in boxes (not shown) or cartons (not shown) for shipping and storage.

An additional advantage of the above-disclosed container shape is that the container 32 can rest on one of its flat surfaces to facilitate insertion of the drug vial 72, and also during storage and transportation after mounting of the drug vial 72, but before actual administration.

The bottles 32, and also the associated structure including the neck or hinge base member 44 and the intermediate member 54, can advantageously be manufactured by injection molding from a suitable medical grade plastic material. In this regard, many different kinds of plastics well known in the art are suitable, medical grade polypropylene and acrylic serve as examples.

The operation, function, and certain advantages of the first preferred embodiment 30 of the apparatus of the present invention should be readily apparent to those skilled in the art from the foregoing description, and are therefore described here only briefly for the sake of complete disclosure. Thus, before reconstituting the solid antibiotic (or other material) contained in the standard small vial 72, a user (such as a laboratory technician, a pharmacist, nurse, or medical doctor) inserts the vial 72 into the intermediate member 54, thereby causing the spike 58 to break through the seal 76, as is shown on FIG. 3. In this position of the vial 72 relative to the bottle 32, however, the antibiotic is not yet exposed to the intravenous fluid 34, and therefore the assembled vial 72 and bottle 32 may be transported, or stored even for a prolonged period of time. In accordance with one contemplated typical use of the invention, the vial 72 is assembled to the bottle 32 in the hospital's pharmacy (not shown), from where it may be transported to the patient (not shown) into a ward or operating room (not shown). Then, just before actual administration to the patient (not shown), the intermediate member 54 is turned so as to establish fluid communication between the bottle 32 and vial 2. Turning the assembly upside down causes the intravenous fluid 34 to flow into the vial 72. Thereafter, the resulting reconstituted antibiotic (or other drug) solution is allowed to flow back into the bottle 32. Having two, rather than just one duct in the spike 58 facilitates this process.

After mixing of the contents of the bottle 32 by slight external agitation, such as shaking, the resulting dilute antibiotic solution is infused to a patient (not shown) through a standard i.v. set (not shown).

Referring now to FIGS. 9 through 13 of the appended drawings, a second preferred embodiment 90 of the apparatus of the present invention is disclosed. Because the second preferred embodiment 90 is similar in certain respects and overall function to the first preferred embodiment 30, it is described here in less detail than the first preferred embodiment 30.

Thus, the bottle or container 32 of the second preferred embodiment includes, on its upper surface 78, a substantially ball-shaped neck member 92. The ball-shaped neck member 92 incorporates a central duct or flow channel 46, leading into the interior of the bottle 32. The overall purpose of the ball-shaped member 92 is substantially the same as that of the neck portion 44 of the first preferred embodiment 30, that is, to serve as a hinge base for the intermediate member. The intermediate member 94 is similar to the intermediate member 54 of the first preferred embodiment 30, except that in the second preferred embodiment 90, the intermediate member 94 includes a substantially spherical cavity 96 through which the intermediate member 94 is pivotably mounted to the ball-shaped neck 92.

FIG. 9 discloses a first position of the intermediate member 94 relative to the bottle 32, wherein the flow channel 46 of the ball-shaped neck 92 is not aligned with the dual ducts 64 and 65 of the spike 58. The intermediate member 94 is removably retained in the first position by a tab or prong 98 and by a matching depression 100 in the ball-shaped neck 92. The tab 98 is rounded so it can act as a smooth camming surface when the positioning of the intermediate member 94 is to be altered.

Figure 10:
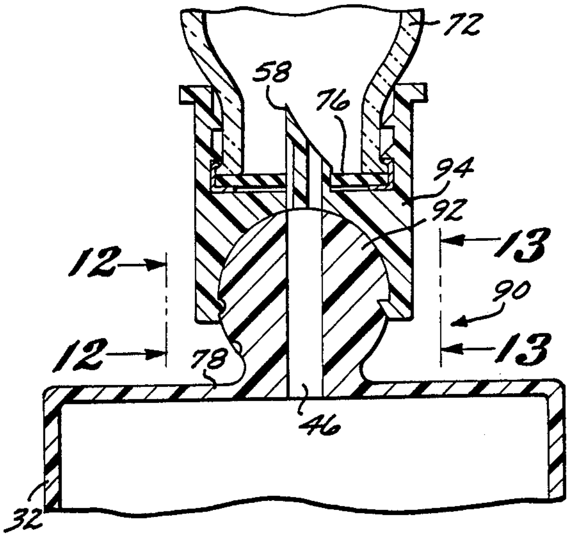
FIG. 10 is a partial cross-sectional view of the second preferred embodiment of the apparatus of the present invention having a standard small vial for antibiotics or the like, mounted to the second preferred embodiment in a second position where there is fluid communication between the intravenous bottle of the second embodiment and the standard vial.
Figure 11:
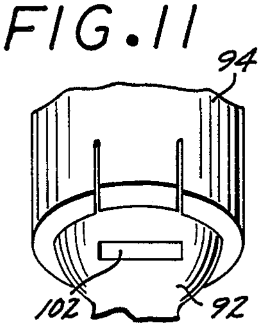
FIG. 11 is a view taken on lines 11,11 of FIG. 9.
Figure 12:
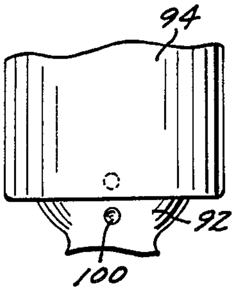
FIG. 12 is a view taken on lines 12,12 of FIG. 10.
Figure 13:
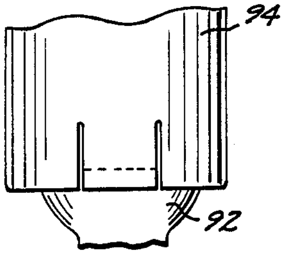
FIG. 13 is a view taken on lines 13,13 of FIG. 10.

FIG. 10 discloses a second position of the intermediate member 94 relative to the bottle or container 32, wherein the flow channel 46 is aligned with the dual ducts 64 and 65. As is apparent from FIG. 10, in this position there is fluid communication between the vial 72 and the bottle 32. The intermediate member 94 and the vial 72 are retained in the second position by another depression 102 and matching tab 104. Once fluid communication has been established between the vial 72 and the bottle 32, the "irreversible" process of reconstituting the antibiotic has begun. Therefore, the tab 104, unlike the tab 98, is sharply angular, whereby it cannot act as a smooth camming surface, and does not permit reversal of the positioning of the intermediate member 94 from the second position of FIG. 10 to the first position of FIG. 9. Thus, the tab 104 and the matching depression 102 in the ball-shaped neck 92 act as means for locking the intermediate member 94 in the second position, where fluid communication is established between the vial 72 and the bottle 32. The same function is served in the first preferred embodiment 30 by the cooperating ratchet teeth 80 and 82.

Figure 14:
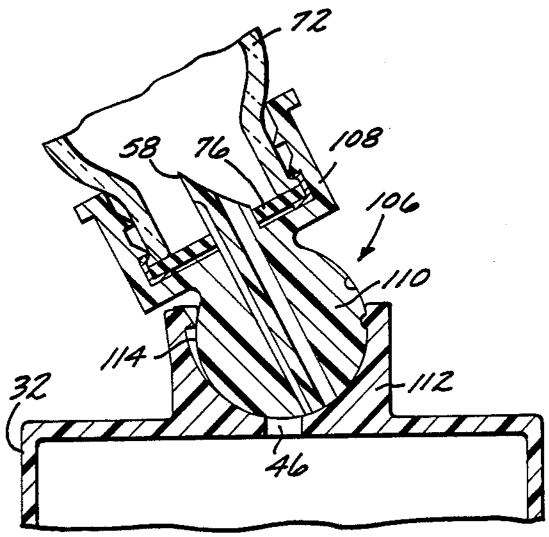
FIG. 14 is a partial cross-sectional view of a third preferred embodiment of the apparatus of the present invention having a standard small vial for antibiotics or the like, mounted to the third preferred embodiment in a first position where there is no fluid communication between the intravenous bottle of the third embodiment and the standard vial.
Figure 15:
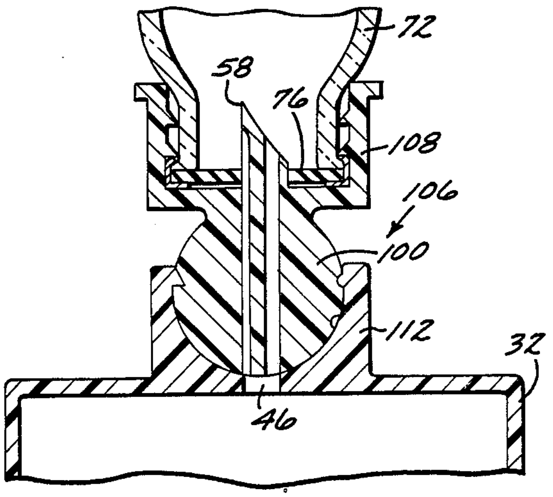
FIG. 15 is a partial cross-sectional view of a third preferred embodiment of the apparatus of the present invention having a standard small vial for antibiotics or the like, mounted to the third preferred embodiment in a second position where there is fluid communication between the intravenous bottle of the third embodiment and the standard vial.
Figure 16:
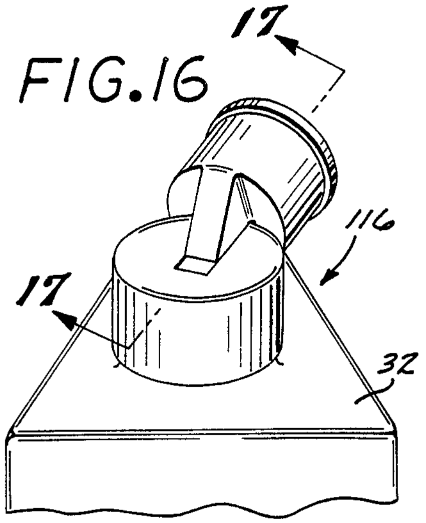
FIG. 16 is a partial perspective view of a fourth preferred embodiment of the present invention.

Referring now to FIGS. 14 and 15, a third preferred embodiment 106 of the invention is disclosed. The third embodiment 106 is similar to the second preferred embodiment 90, except that in the third embodiment 106 the intermediate member 108 includes a substantially spherical joint 110, and the neck member 112 of the bottle 32 includes a matching cavity 114 to accept the joint 110.

FIGS. 16 through 21 disclose a fourth preferred embodiment 116 of the apparatus of the present invention. In this embodiment 116, the bottle 32 has a cylindrical neck 118. A cap member 120 is threaded to the cylindrical neck 118. The cap member 120 is configured so as to accept the pivotable mounting of a spike 58 containing intermediate member 122. To this end, the cap member 120 includes an opening 124 and a space of concave curvature 126 to accept a substantially cylindrical joint 128 of the intermediate member 122.

Figure 17:
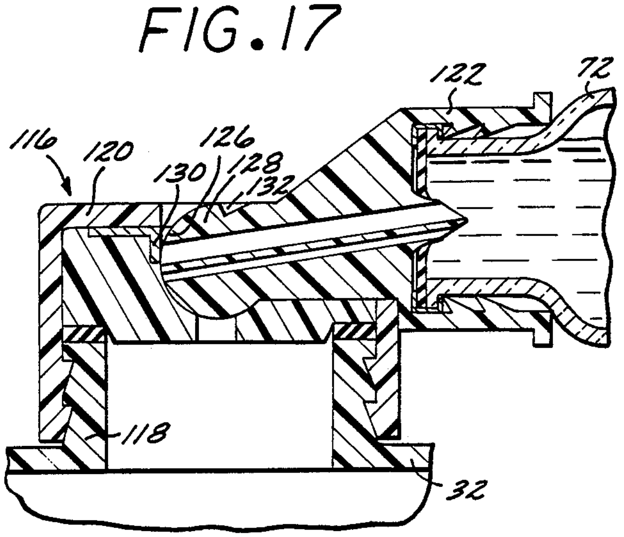
FIG. 17 is a partial cross-sectional view of a fourth preferred embodiment of the apparatus of the present invention having a standard small vial for antibiotics or the like, mounted to the fourth preferred embodiment in a first position where there is no fluid communication between the intravenous bottle of the fourth embodiment and the standard vial, the view being analogous to a view taken on lines 17,17 of FIG. 16.
Figure 18:
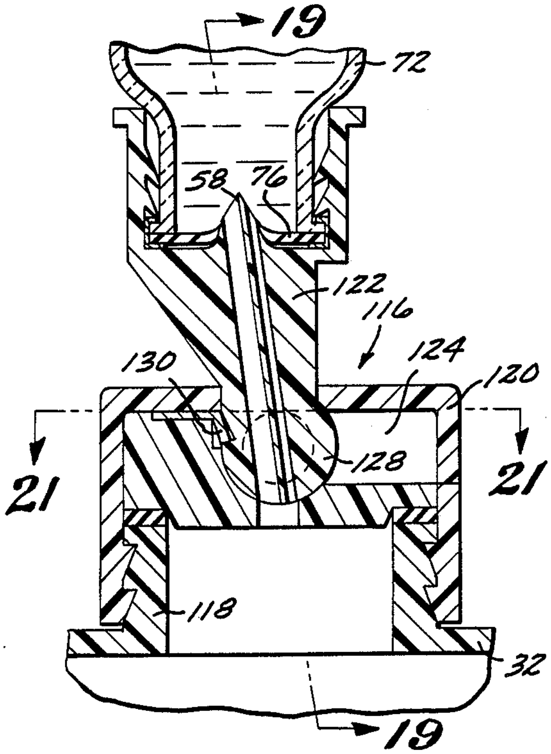
FIG. 18 is a partial cross-sectional view of a fourth preferred embodiment of the apparatus of the present invention having the standard small vial for antibiotics or the like, mounted to the fourth preferred embodiment in a second position where there is fluid communication between the intravenous bottle of the fourth embodiment and the standard vial.
Figure 19:
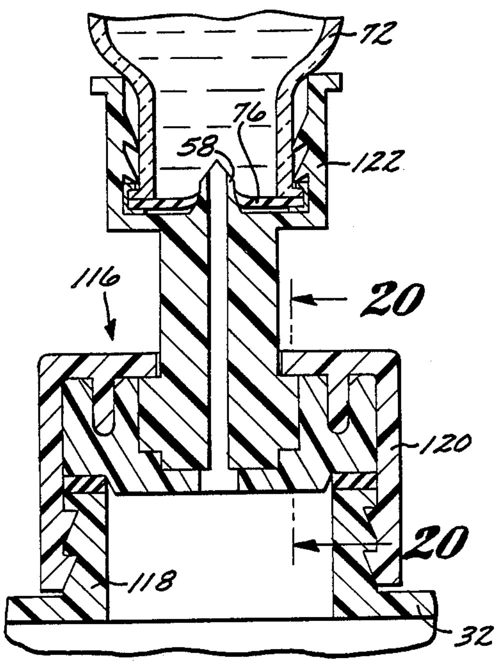
FIG. 19 is a cross-sectional view taken on lines 19,19 of FIG. 18.
Figure 20:
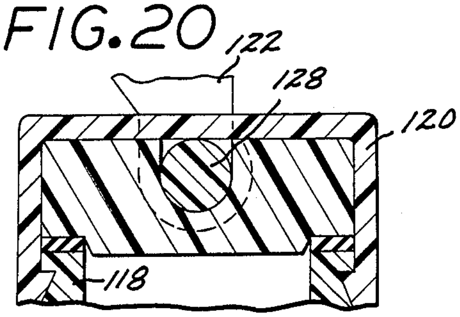
FIG. 20 is a cross-sectional view taken on lines 20,20 of FIG. 19.
Figure 21:
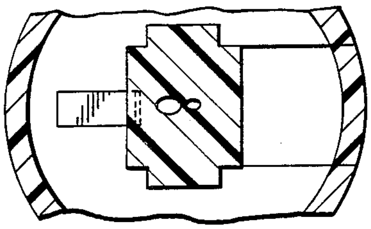
FIG. 21 is a cross-sectional view taken on lines 21,21 of FIG. 18.

FIG. 17 shows the intermediate member 122 and an antibiotic vial 72 in a first position relative to the bottle 32, wherein there is no fluid communication between the bottle 32 and the vial 72.

FIGS. 18 through 21 show a second position of the intermediate member 122 relative to the bottle 32, wherein there is fluid communication between the bottle 32 and vial 72. A tab 130, incorporated in the cap member 120, and a matching depression 132 in the cylindrical joint 128, lock the intermediate member 122 in the second position so that once the process of reconstituting the antibiotic has been started, the possibility of inadvertent error regarding the status of the contents of the vial 72 is eliminated or at least minimized.

Several further modifications of the apparatus of the present invention may become readily apparent to those skilled in the art in light of the foregoing disclosure. Therefore, the scope of the present invention should be interpreted solely from the following claims, as such claims are read in light of the disclosure.

What is claimed is:

1. An apparatus adapted for use in storing an intravenous fluid, mixing the intravenous fluid with a second ingredient, and for intravenously administering the intravenous fluid mixed with the second ingredient to a patient, the apparatus comprising:

a first container for the intravenous fluid, the first container having a first opening sealed with a first pierceable membrane whereby the first membrane may be penetrated with a sharp spike of a secondary intravenous set to drain, in the process of administering said fluid to a patient, the intravenous fluid from the container, the container having a second opening, and first means operatively associated with the second opening for capturing and fixedly holding the neck of a second substantially standard container for antibiotic powders and the like of the type having a pierceable second membrane seal and a metal band affixing the second membrane seal to the neck of the second container, the first means being adapted for piercing the second membrane seal of the second container without establishing fluid communication between the first and second containers while the second container is fixedly held by the first means in a first position thereof, and for establishing fluid communication between the first and second containers in a second position of the second container relative to the first container, the relative position of the second container to the first container being changeable from the first position to the second position at the option of an operator by a pivoting motion of the first means, whereby the intravenous fluid of the first container may be admixed with the contents of the second container and the admixed fluid may be returned to the first container for administration to a patient.

2. The apparatus of claim 1 wherein the first means further comprise means for locking the second container into the second position after the second container has been placed into said second position.

3. The apparatus of claim 2 wherein the first means include a hinge base immovably attached to the first container and a duct in the hinge base which comprises the second opening, and a member mounted to the hinge base for limited pivoting motion relative to the hinge base, the member including a spike having at least one interior duct, the interior duct of the spike not being aligned with the second opening in the first position of the second container and being aligned with the second opening in the second position of the second container, whereby in the second position of the second container there is fluid communication between the first and second containers through the interior ducts of the hollow spike and the second opening.

4. The apparatus of claim 3 wherein the member mounted to the hinge base has a substantially cylindrical tubular portion which surrounds the hollow spike and the interior substantially cylindrical wall of which includes at least one circumferential rib forming part of the first means for holding the neck of the second container.

5. The apparatus of claim 4 wherein the interior substantially cylindrical wall of the member includes at least two spaced, circumferential ribs, one of said ribs being configured for engaging the back rim of the mouth of the second container.

6. The apparatus of claim 5 wherein the means for locking the second container into the second position comprise a plurality of meshing ratchet teeth attached to the container and to the member mounted to the hinge base, respectively.

7. The apparatus of claim 5 wherein the hinge base is a substantially cylindrical member, and wherein the member attached to the hinge base has a second tubular portion mating with and being pivotably attached to the cylindrical member of the hinge base.

8. The apparatus of claim 5 wherein the hinge base is a substantially ball-shaped body and wherein the member attached to the hinge base has a cavity of substantially spherical curvature, the cavity mating with the ball-shaped body.

9. The apparatus of claim 8 wherein the means for locking the second container into the second position comprise a plastic tooth and a matching opening adapted for engaging the tooth, placed respectively in the member and in the ball-shaped hinge base.

10. The apparatus of claim 5 wherein the hinge base is a substantially cylindrical body including an opening of substantially spherical curvature, and wherein the member attached to the hinge base includes a substantially ball-shaped body mating with and mounted into the opening of spherical curvature.

11. The apparatus of claim 10 wherein the means for locking the second container into the second position comprise a plastic tooth and a matching opening adapted for engaging the tooth, placed respectively in the hinge base and in the ball-shaped body mating with the hinge base.

12. An apparatus adapted for use in storing an intravenous fluid, mixing the intravenous fluid with a second ingredient such as an antibiotic powder, for the purpose of substantially immediate intravenous administration to a patient, the apparatus comprising:

- a first elongated container for the intravenous fluid, the first container having a first opening sealed with a first pierceable membrane and comprising means for permitting penetration with a sharp spike of a secondary intravenous set to drain, in the process of administering said fluid to a patient, the intravenous fluid from the container, the container having a second opening disposed substantially at the opposite end of the elongated container from the first opening;
- a first member fixedly attached to the exterior of the first container to surround the second opening, the member comprising means for receiving and pivotably holding an intermediate member, and
- a tubular member mounted to the first member to occupy two extreme positions relative thereto, the tubular member comprising first means for holding by its neck portion a second substantially standard container for antibiotic powders and the like of the type having a pierceable second membrane seal and a metal band affixing the second membrane seal to the neck portion of the second container, the tubular member further comprising hollow spike means for piercing the second membrane seal, the hollow spike means having an interior duct, in the first extreme position the interior duct of the spike means not being aligned with the second opening whereby in the first extreme position there is no fluid communication between the first and second containers, in the second extreme position the interior duct of the spike means being aligned with the second opening whereby in the second extreme position there is fluid communication between the first and second containers so that the intravenous fluid of the first container may reconstitute the antibiotic of the second container.

13. The apparatus of claim 12 wherein the hollow spike means has two interior ducts fluidly connecting the first and second containers in the second extreme position.

14. The apparatus of claim 12 wherein the first container has a substantially triangular cross-section in a plane perpendicular to the longitudinal axis of the first container.

15. The apparatus of claim 12 further comprising means for substantially preventing the repositioning of the tubular member from the second extreme position to the first extreme position.

16. The apparatus of claim 15 wherein the first means comprise a pair of substantially parallel spaced ribs disposed in the interior wall of the tubular member.

17. An apparatus adapted for use in storing an intravenous fluid, and storing a medicinal ingredient, such as an antibiotic powder, separately from the intravenous fluid, mixing the intravenous fluid with the second ingredient as in the process of reconstituting the antibiotic powder for the purpose of substantially immediate intravenous administration to a patient, the apparatus comprising in combination:

- a first elongated container for the intravenous fluid, the first container having a first opening sealed with a first pierceable membrane and comprising means for permitting penetration with a sharp spike of a secondary intravenous set to drain, in the process of administering said fluid to a patient, the intravenous fluid from the container, the container having a second opening disposed substantially at the opposite end of the elongated container from the first opening;
- a first member fixedly attached to the exterior of the first container to surround the second opening;
- a tubular member mounted to the first member to occupy a first and a second extreme position relative to the first member and to the first container, the first member comprising means for receiving and pivotably holding the tubular member;
- a second substantially standard container for antibiotic powders and the like of the type having a pierceable second membrane seal and a metal band affixing the second membrane seal to the neck of the second container, the tubular member comprising first means for holding the second container by its neck, the tubular member further comprising hollow spike means for piercing the second membrane seal, the hollow spike means having an interior duct, in the first extreme position the interior duct of the spike means not being aligned with the second opening whereby in the first extreme position there is no fluid communication between the first and second containers, in the second extreme position the interior duct of the spike means being aligned with the second opening whereby in the second extreme position there is fluid communication between the first and second containers so that the intravenous fluid of the first container reconstitutes the contents of the second container.

18. The apparatus of claim 17 wherein the hollow spike means has two interior ducts fluidly connecting the first and second containers in the second extreme position.

19. The apparatus of claim 17 wherein the first container has a substantially triangular cross-section in a plane perpendicular to the longitudinal axis of the first container.

20. The apparatus of claim 17 further comprising means for substantially preventing the repositioning of the tubular member from the second extreme position to the first extreme position.

21. The apparatus of claim 20 wherein the means for substantially preventing comprise interlocking ratchet teeth incorporated into the first member and the tubular member.

22. The apparatus of claim 17 wherein the first means comprise a pair of substantially parallel spaced ribs disposed in the interior wall of the tubular member.

23. The apparatus of claim 17 wherein the first member is a substantially cylindrical member having circumferential ribs, and wherein the tubular member attached to the first member has in its interior a surface mating with said circumferential ribs, whereby the tubular member is pivotable about the longitudinal axis of the cylindrical member.

24. The apparatus of claim 17 wherein the first member includes a substantially ball-shaped body and wherein the tubular member attached to the first member includes a portion having a cavity of substantially spherical interior curvature, the cavity mating with the ball-shaped body.

25. The apparatus of claim 17 wherein the first member is a body including a cavity of substantially spherical curvature, and wherein the tubular member attached to the first member includes a substantially ball-shaped body mating with and mounted into the cavity.

26. The apparatus of claim 25 wherein the first member is a body including a cavity of substantially cylindrical curvature, and wherein the tubular member attached to the first member includes a section mating within the cavity of cylindrical curvature.

* * * * *

UNITED STATES PATENT AND TRADEMARK OFFICE
CERTIFICATE OF CORRECTION

PATENT NO. : 4,735,608

DATED : April 5, 1988

INVENTOR(S) : William W. Sardam

It is certified that error appears in the above-identified patent and that said Letters Patent is hereby corrected as shown below:

Column 8, line 30, change "2" to --72--.

Signed and Sealed this

Seventeenth Day of January, 1989

*Attest:*

DONALD J. QUIGG

*Attesting Officer*

*Commissioner of Patents and Trademarks*